United States Patent
Hamel et al.

(10) Patent No.: US 6,669,432 B2
(45) Date of Patent: Dec. 30, 2003

(54) APPARATUS AND METHOD FOR HANDLING PIPETTING TIP MAGAZINES

(75) Inventors: Marc Hamel, Hudson, NH (US); Greg Mathus, Concord, MA (US); Michael F. LaCourse, East Waterboro, ME (US); Robert H. Hunt, Kennebunk, ME (US); Mark Dumont, Saco, ME (US)

(73) Assignee: Matrix Technologies Corp., Hudson, NH (US)

( * ) Notice: Subject to any disclaimer, the term of this patent is extended or adjusted under 35 U.S.C. 154(b) by 20 days.

(21) Appl. No.: 09/928,782

(22) Filed: Aug. 13, 2001

(65) Prior Publication Data

US 2003/0031542 A1 Feb. 13, 2003

(51) Int. Cl.$^7$ ............................................. G01N 35/02
(52) U.S. Cl. ........................... 414/331.05; 414/222.01; 422/100
(58) Field of Search .................... 414/331.05, 331.09, 414/403, 806, 810, 222.01; 422/100, 64, 103, 104; 436/49

(56) References Cited

U.S. PATENT DOCUMENTS

| | | | |
|---|---|---|---|
| 3,708,264 A | 1/1973 | Jottier | |
| 4,187,077 A | 2/1980 | Covington et al. | |
| 4,676,951 A | * 6/1987 | Armes et al. | 422/65 |
| 5,061,639 A | 10/1991 | Lung et al. | |
| 5,233,844 A | 8/1993 | Knippscheer et al. | |
| 5,285,333 A | 2/1994 | Barr et al. | |
| 5,507,410 A | 4/1996 | Clark et al. | |
| 5,607,275 A | 3/1997 | Woodruff et al. | |
| 5,653,942 A | 8/1997 | Terashima et al. | |

(List continued on next page.)

OTHER PUBLICATIONS

CyBio Brochure, CyBi™–Screen–machine, One System—Many solutions, pp. 1–20, 2000.

CyBio (printout from website), Automatic tip changer for the simultaneous pipetter CyBi™–Well, Aug. 9, 2001.

*Primary Examiner*—Eileen D. Lillis
*Assistant Examiner*—Charles A Fox
(74) *Attorney, Agent, or Firm*—Wolf, Greenfield & Sacks, P.C.

(57) ABSTRACT

A method and apparatus for automatically removing used magazines with used pipette tips from a pipetting head in an automated pipettor, and for automatically inserting an unused or cleaned magazine with unused or cleaned pipette tips in their place. The apparatus includes a gripping mechanism having two separate and independently operated gripping heads, one gripping head being associated exclusively with unused or cleaned magazines and pipetting tips, and the other gripping head being associated exclusively with used magazines and pipette tips. A transporting mechanism is provided for moving the gripping heads between the pipetting head, a disposal mechanism, and a supply of unused or cleaned magazines and pipetting tips. The supply preferably includes a carousel with a multiplicity of locations for storing unused or cleaned magazines and tips in a vertical alignment. The carousel is rotated so that a compartment containing unused or cleaned magazines and tips is in alignment with an opening in the carousel. The gripping head automatically scans the carousel looking for the next available unused or cleaned magazine and tips for transport to the pipetting head. Another scanning mechanism locates the used magazine in the pipetting head for removal. The method includes the steps of withdrawing a used magazine and tips from a pipetting head, inserting unused or cleaned magazine and tips in the pipetting head, and transporting the used magazine and tips to a disposal location. The method also includes the step of automatically retrieving unused or cleaned magazines and tips from a storage location for transport to the pipetting head.

23 Claims, 13 Drawing Sheets

U.S. PATENT DOCUMENTS

| | | | |
|---|---|---|---|
| 5,928,952 A | * 7/1999 | Hutchins et al. | 436/50 |
| 5,993,045 A | * 11/1999 | Schmidtke et al. | 700/214 |
| 6,008,964 A | * 12/1999 | Goodknight et al. | 360/92 |
| 6,182,719 B1 | 2/2001 | Yahiro | |
| 6,255,116 B1 | 7/2001 | Leber et al. | |
| 6,258,324 B1 | 7/2001 | Yiu | |
| 6,299,840 B1 | 10/2001 | Watanabe et al. | |
| 6,325,114 B1 | * 12/2001 | Bevirt et al. | 141/130 |
| 6,358,470 B1 | 3/2002 | Higuchi | |
| 6,360,792 B1 | 3/2002 | Ganz et al. | |
| 6,372,185 B1 | 4/2002 | Shumate et al. | |
| 6,395,231 B1 | 5/2002 | Kraemer et al. | |
| 6,399,024 B1 | 6/2002 | Bevirt et al. | |
| 6,464,943 B1 | * 10/2002 | Yiu | 422/100 |
| 2001/0005489 A1 | 6/2001 | Roach et al. | |
| 2001/0039843 A1 | 11/2001 | Schoeppe | |
| 2002/0104389 A1 | 8/2002 | Hovey | |

\* cited by examiner

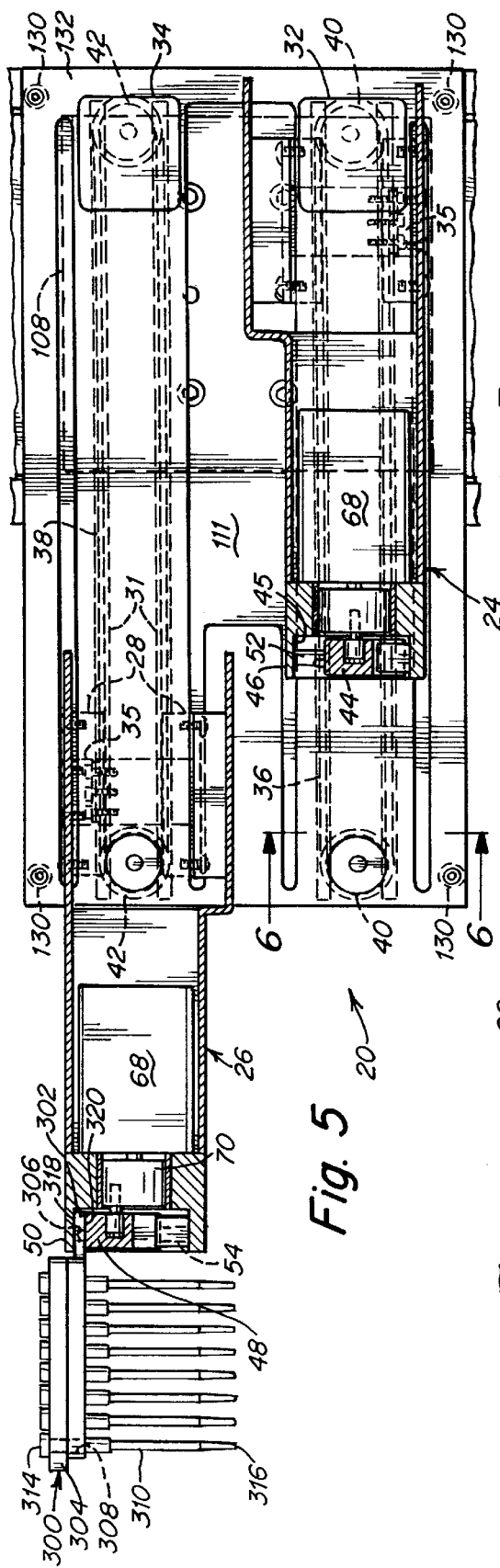
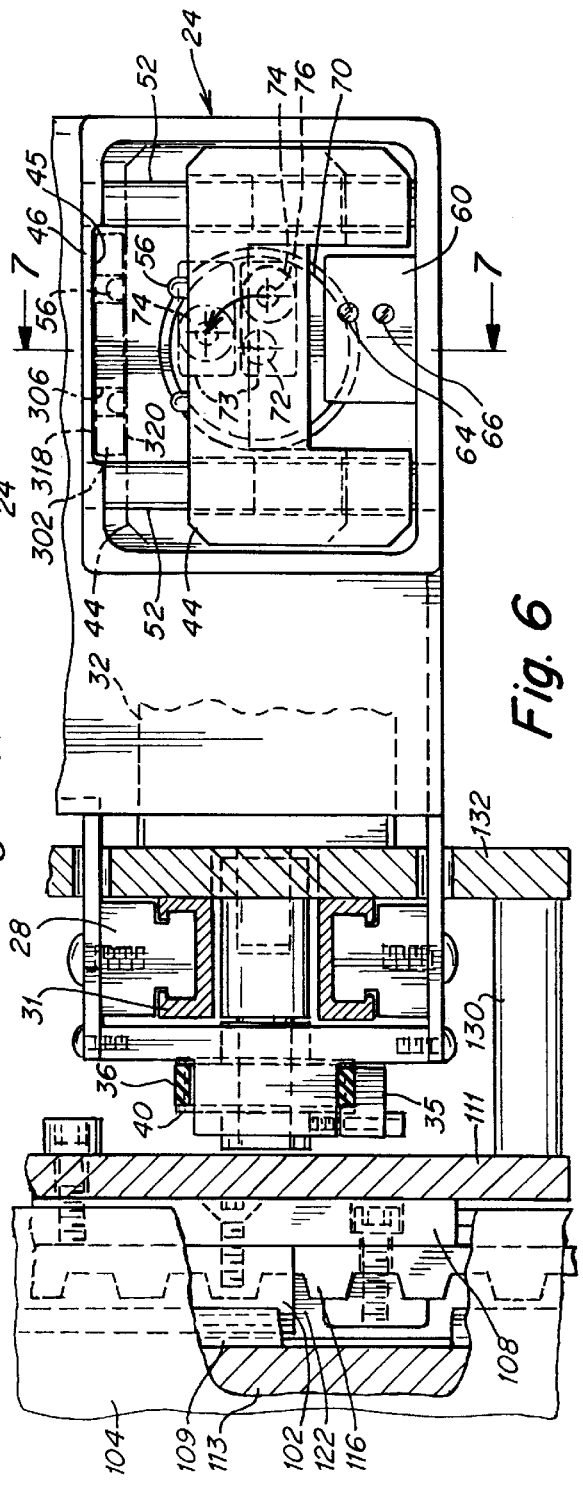
Fig. 5
Fig. 6

APPARATUS AND METHOD FOR HANDLING PIPETTING TIP MAGAZINES

FIELD OF THE INVENTION

This invention relates generally to liquid transfer and dispensing devices for liquid reagents and samples, and more particularly to an automated apparatus and method for handling magazines containing pipetting tips.

BACKGROUND OF THE INVENTION

Pipetting systems are well known, and typically are used in laboratories and hospitals for the aspiration and dispensing of relatively small, predetermined quantities of liquids into the wells of plates such as microplates, deep-well blocks and the like. Examples of liquids being dispensed include blood, other biological samples, solvents, reagents, and the like. Some or all of the liquid is normally drawn by suction through pipette tips from one set of plates or a reservoir of liquid and is subsequently released through the pipette tips into the wells of other plates.

Not all plates have the same well spacings, and not all plates have the same number of wells. Therefore, it is desirable to vary the number of pipette tips, or the spacings between tips in such automated systems to accommodate plates with different well numbers and spacings. Moreover, it is desirable to be able to replace used pipette tips with unused ones. Such flexibility is essential in most laboratories and hospitals. It is also desirable to be able to perform such operations rapidly, and to be able to perform a high volume of operations in a very short period of time.

In existing high volume, automated, multichannel pipetting systems, typically trays or magazines of disposable pipette tips are positioned in the dispensing head of the pipettor. Such magazines are configured to support a predetermined number of tips of a certain size and with a defined spacing. Each pipette tip has an enlarged upper end which is configured to be engaged in sealing relation to with an apparatus for aspirating liquid into the tip and expelling it therefrom. The lower end of each tip is tapered and has an opening through which liquid in a well of a microplate or a supply reservoir is withdrawn and expelled. Typically, these magazines are removable from the dispensing head of the pipetting apparatus to allow replacement of one magazine of pipette tips with another to prevent contamination of liquid from one pipetting operation with that of another pipetting operation. These tips may either be disposed of or washed for future pipetting operations. In some existing, automated pipetting apparatus, the magazines containing tips are manually replaced, while in others, the insertion and removal of magazines is accomplished in an automatic or semi-automatic fashion. These exchanges should be performed rapidly and automatically to maintain a high throughput, and to minimize needed operator time. Automated systems performing such exchanges must be able to interface with existing automated pipetting systems.

An example of an automated pipetting system which uses magazines containing pipette tips is disclosed in co-pending U.S. application Ser. No. 09/865,404, filed May 25, 2001, and assigned to the Assignee of the present application. Other automated, high volume systems include those shown in U.S. Pat. Nos. 4,830,832; 6,148,878; and 5,988,236. An example of an existing automated pipette tip changer is sold by Cybio AG of Jena, Germany.

SUMMARY OF THE INVENTION

The present invention relates to a method and apparatus for handling magazines containing pipetting tips and is used in conjunction with high volume, automated pipetting systems. In particular, the present invention is used with automated pipetting systems which have a dispensing head configured to receive a magazine of pipette tips in which one magazine of used or inappropriately sized tips can be replaced with another magazine of unused or appropriately sized tips.

One aspect of the invention relates to a magazine handling apparatus having one or more gripper heads for gripping a magazine. These gripper heads are associated with a transfer apparatus which moves the gripper heads from a dispensing head of a pipettor to a location for disposal of used magazines containing pipette tips, and from a source of unused magazines containing unused pipette tips to the dispensing head of the automated pipettor. In one embodiment of this aspect, two gripper heads are disclosed, and one gripper head is configured to grip only a used magazine with used pipette tips and convey the used magazine from the pipettor to a disposal location. The other gripper head is configured to grip only an unused magazine with unused tips and convey the unused magazine from a source of unused magazines to the dispensing head of the pipettor. In another embodiment of this invention, the two gripper heads are disposed vertically, one above the other, with the upper gripper head being the gripper configured only to grip unused magazines, while the lower gripper head is configured to only grip used magazines with used pipette tips.

In another embodiment of this aspect of the invention, each gripper head includes a sensor which senses a particular location on a tip magazine to align the gripper head with the magazine. In particular, in a preferred embodiment, the location sensed is a tab or handle on the magazine which is to be grasped by the gripper head. Preferably, the sensor is a converging, diffuse, reflective sensor which has a controlled depth of field.

In another aspect of the invention, the source of unused tips and magazines is a carousel accessible by a gripper head. In one embodiment, the carousel includes a plurality of stacker assemblies each of which is configured to contain a plurality of magazines and associated pipette tips. Each stacker assembly is removable from the carousel for filling thereof with magazines and tips, and each stacker assembly is replaceable into the carousel when filled with magazines and tips. Each stacker assembly has an open side which may be aligned with an opening in the carousel which is accessible by a gripper head. In another embodiment, the carousel is automatically rotated until a source of unused magazines and tips is disposed adjacent the opening accessible by the gripper head. In yet another embodiment of this aspect, the carousel is disposed vertically below the dispensing head on the automated pipetting system.

In another aspect of the invention, a method is provided for automatically removing used or dirty magazines and pipette tips from the dispensing head of an automated pipetting system, and replacing the used magazine with an unused magazine with unused tips. In one embodiment of this aspect, the method includes the steps of removing the used magazine from the dispensing head using an automated gripper, inserting an unused magazine in the dispensing head in place of the used magazine, and conveying the used magazine to a disposal location. In one embodiment of this method, two gripper heads are used, and one gripper head carries only unused magazines and the other gripper head carries only used magazines. In a further embodiment, the one gripper head carries an unused magazine ready for insertion into the dispensing head prior to the removal of the used magazine by the other gripper head, so that the unused magazine is inserted upon removal of the used magazine.

Preferably, in this embodiment, the gripper head holding the unused magazine is disposed above the gripper head holding the used magazine, so that the unused magazine is not contaminated by the used magazine.

In a further embodiment of the method of this invention, clean, unused magazines are stored in a carousel in a stacked array. The gripper head searches for the next available magazine, retrieves it from an opening in the carousel, and returns to the dispensing head to await completion of the pipetting operation, and removal of the used magazine. In this embodiment of the method, the magazines may be stored in a stacker which can be retrieved from the carousel and replaced after being filled with new, unused magazines and tips. The carousel may be automatically rotated to a position such that a stacker containing unused magazines is presented to an opening which can be accessed by the gripper head. In another embodiment of the method, the carousel is disposed vertically below the dispensing head in the automated pipettor.

The foregoing method and apparatus permit rapid, accurate and automated replacement of pipette tip magazines in the dispensing head of an automated pipettor.

BRIEF DESCRIPTION OF THE DRAWINGS

The objects, advantages and features of this invention will be more clearly appreciated from the following detailed description, when taken in conjunction with the accompanying drawings in which:

FIG. 5 is a cross-sectional, side view of the upper and lower gripper heads taken along the line 5—5 of FIG. 4;

FIG. 6 is a front elevational view of a gripper head as seen along line 6—6 of FIG. 5;

DETAILED DESCRIPTION

Figure 1:
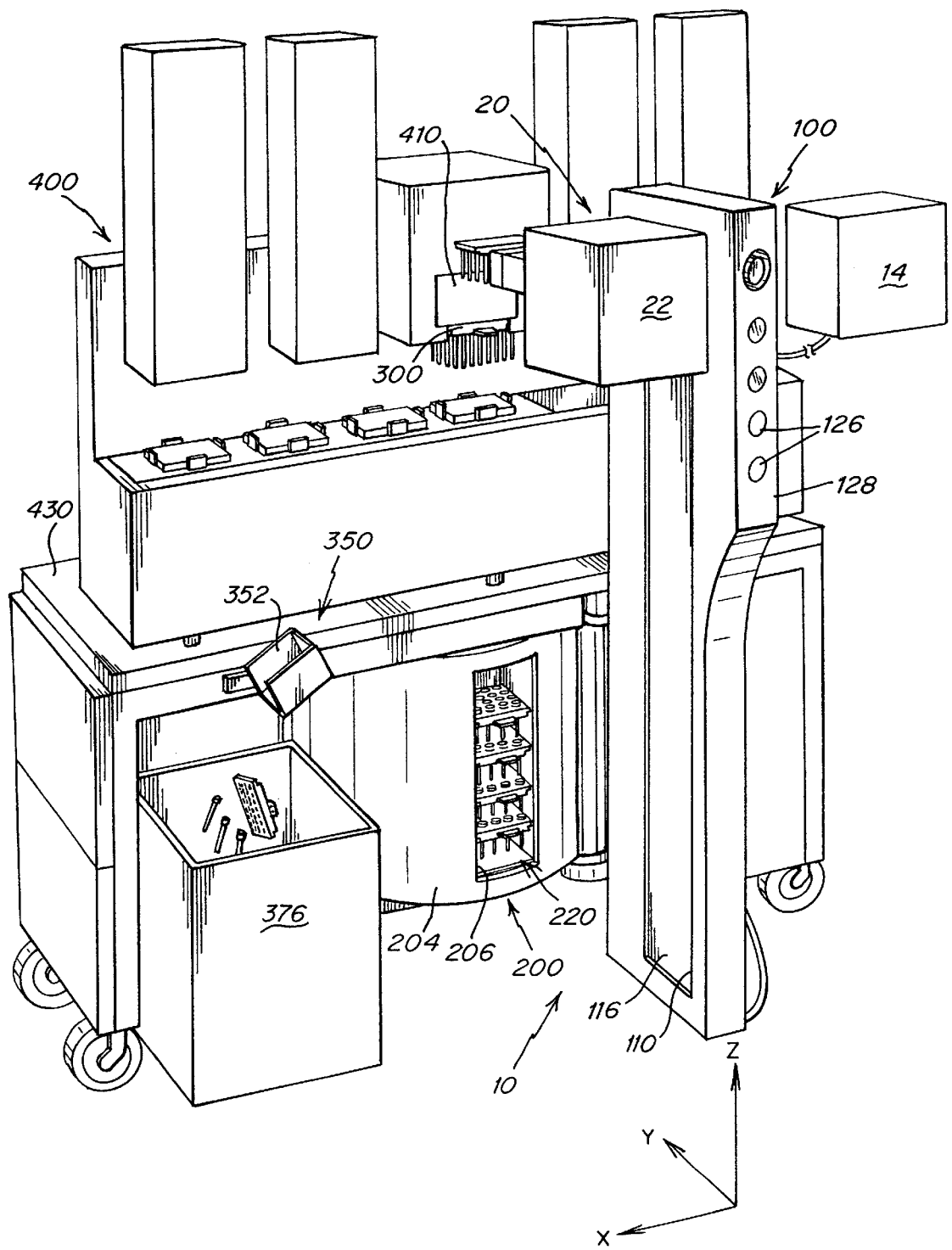
FIG. 1 is a perspective view illustrating the apparatus of this invention for handling pipette tip magazines in conjunction with an automated pipettor.
Figure 2:
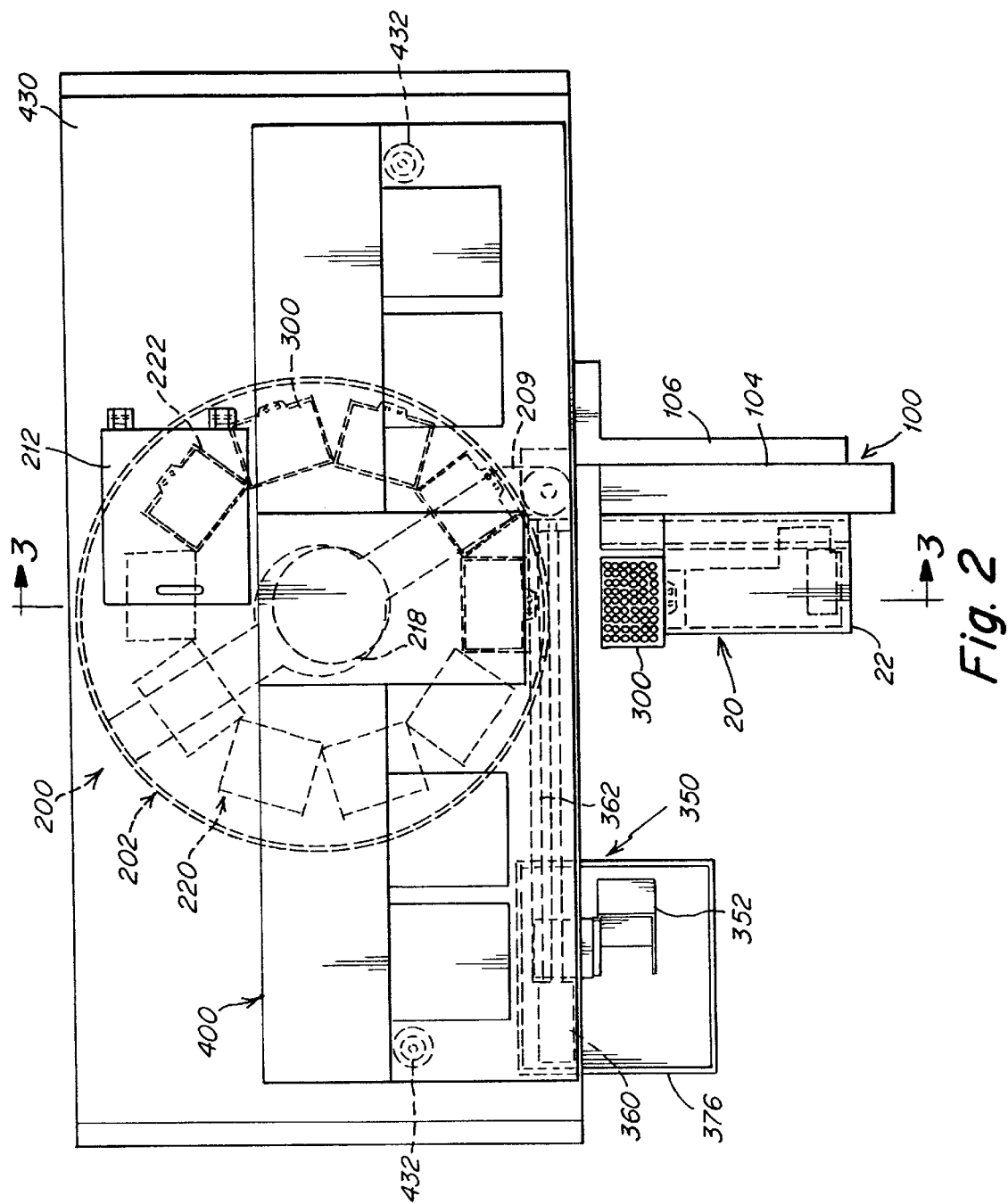
FIG. 2 is a top plan view of the apparatus of FIG. 1.

With reference now to the drawings, and more particularly to FIGS. 1 and 2 thereof, the pipette tip magazine handling apparatus 10 of this invention will now be described. In a preferred embodiment, apparatus 10 includes a gripper assembly 20, a gripper transport mechanism 100 and a magazine supply 200. Gripper assembly 20 is configured to interact with an automated pipetting system 400 having a pipette dispensing head 410. Dispensing head 410 includes a clamp 420 (see FIG. 3) or other like device for holding a pipette tip magazine 300 in head 410 during the pipetting operation. A sensor 440 indicates the position of clamp 420 and is electrically coupled to apparatus 10 (See FIG. 3).

Each pipette tip magazine 300 typically includes a body 304 and a handle or tab 302. Body 304 includes a plurality of sleeves 308, each of which supports or is configured to support a pipette tip 310 within it (See FIG. 5). Typically, body 304 of magazine 300 is formed of a molded plastic material. However, body 304 may also be formed of metal or any other material which provides sufficient strength, is not breakable, and can withstand high temperatures. In a preferred embodiment, body 304 is formed of a material which is sufficiently inexpensive that magazines 300 can be disposed of after one use. Tips 310 may be any conventional pipette tips which are tapered from an upper end 314 having an enlarged opening to a lower, distal end 316 having a smaller opening (See FIG. 5). Typically, upper end 314 is placed in airtight, fluid communication with a seal 450 surrounding an opening of a piston chamber or the like which withdraws air from tip 310 to aspirate liquid through the lower end 316 of tip 310 and forces air into tip 310 to expel liquid from tip 310 through lower end 316. Seal 450 provides an air tight seal between the upper end 314 of tips 310 and the dispensing head, to provide accurate, error-free pipetting. In one embodiment, seal 450 is a silicone or other like sealing layer. In an alternative embodiment, upper ends 314 of tip 310 could be urged into tight, sealing engagement with nozzle ends (not shown) protruding downwardly from dispensing head 410 for providing the necessary air- and liquid-tight seal with the dispensing head. Lower end 316 typically is placed into a well in a microplate or into a supply reservoir for aspirating liquid therefrom and later transferring that aspirated liquid to another well in a different microplate (not shown). These latter features are all conventional and well known in the art, and will not be described further.

Figure 7:
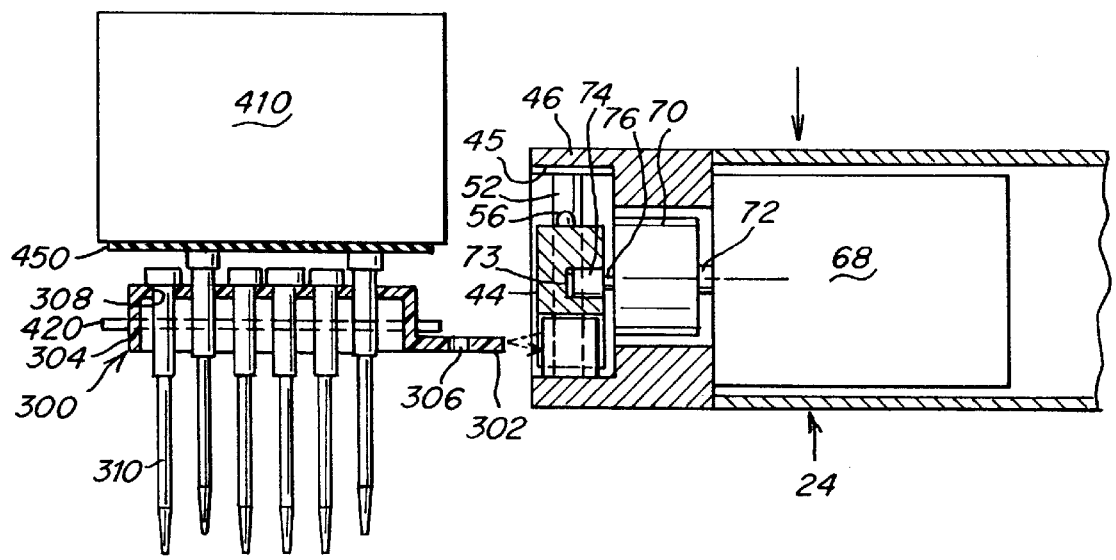
FIG. 7 is a cross-sectional side view of the gripper head taken along line 7—7 of FIG. 6.

Tab 302 extends outwardly from one edge of body 304 of magazine 300. Tab 302 contains relatively flat upper and lower surfaces 318 and 320 respectively. Disposed in lower surface 320 of tab 302 are one and preferably two holes 306 (See FIG. 7), the purpose of which will be described hereinafter.

Typically, pipetting system 400 rests on a table 430 or other like support surface to place system 400 at a level convenient for operation of apparatus 10 and for observation of the pipetting operation. However, system 400 need not be disposed on a table 430, and it may be disposed at some much more elevated position.

For accurate operation of apparatus 10 of this invention, automated pipetting system 400 must be precisely and fixedly disposed with respect to apparatus 10. Preferably, system 400 is bolted or in some other way fixedly attached to table 430 to prevent movement of system 400 with respect to apparatus 10 during operation. In one embodiment, mounts 432 are fixedly positioned on table 430 such as by bolts or screws 433, and system 400 is removably attached to mounts 432 such as by screws 435, so that system 400 can be removed from table 430, to allow system 400 to be exchanged with another system 400 or to be removed for maintenance or repair. Mounts 432 allow system 400 to be returned to table 430 in the precise position desired. In this way, system 400 need not be repositioned every time it is replaced, repaired or maintained.

In this application, for purposes of illustration only, the pipette tip magazine handling apparatus 10 of this invention will be described in conjunction with an automated pipetting system described in U.S. copending application Ser. No. 09/865,404 filed on May 25, 2001, entitled AUTOMATED PIPETTING SYSTEM, and assigned to the Assignee of the present application. U.S. application Ser. No. 09/865,404 is hereby specifically incorporated herein by reference. However, it is to be understood, that the pipette tip magazine handling apparatus 10 of this invention is not limited to use with the automated pipetting system disclosed in U.S. application Ser. No. 09/865,404 but may be used in conjunction with other types of automated pipetting systems. The automated pipetting system of U.S. application Ser. No. 09/865,404 forms no part of this invention.

As shown in FIGS. 3, 4, 7 and 8, gripper assembly 20 is mounted on slideways 102 on gripper transport mechanism 100. Gripper transport mechanism 100 moves gripper assembly 20 on a path extending from magazine supply 200 to a position adjacent dispensing head 410. The operation of gripper assembly 20, gripper transport mechanism 100 and magazine supply 200 is controlled by a personal computer or programmable processor 14.

Gripper assembly 20 will now be described with particular reference to FIGS. 3–7. Gripper assembly 20 includes a housing 22. Disposed within housing 22 are one, and preferably two gripper heads 24 and 26. Each gripper head 24 and 26 rides on an associated set of slides 28 which move along rails 31 and which allow gripper heads 24 and 26 to move in a generally horizontal direction in and out of housing 22 toward dispensing head 410 or toward magazine supply 200. Gripper heads 24 and 26 are each independently moved along associated slides 28 and rails 31 by associated motors 32 and 34 respectively. Heads 24 and 26 are coupled to associated chains 36 and 38 respectively by a belt clamp 35. Chains 36 and 38 ride over associated respective pairs of sprocket wheels 40 and 42. Motor 32 is coupled to one of sprocket wheels 40 for moving chain 36 and thus head 24, and motor 34 is coupled to one of sprocket wheels 42 for moving chain 38 and thus head 26.

In a preferred embodiment, gripper heads 24 and 26 are vertically disposed one above the other to provide a more compact arrangement. However, it is to be understood, that gripper heads 24 and 26 could be aligned in a side-by-side relationship, or, only a single gripper head could be used. An advantage of gripper heads 24 and 26 being aligned one above the other is that transport mechanism 100 need not be moved horizontally or in the X-direction as shown in FIG. 1, with respect to pipetting system 400 when two heads are used. The only movement required of gripper assembly 20 is vertically or in the Z-direction as shown in FIG. 1, along transport mechanism 100.

Each gripper head 24 and 26 has an associated pair of spaced jaws 44, 46 and 48, 50. Preferably, each lower jaw 44 and 48 is moveable with respect to associated stationary upper jaw 46 and 50. Jaws 44 and 48 ride on respective guide shafts 52 and 54. Preferably, although not necessarily, each lower jaw 44 and 48 includes a pair of upstanding pins 56 which are configured to engage corresponding holes 306 in tabs 302 of magazines 300. When lower jaws 44 and 48 are raised against respective upper jaws 46 and 50, tab 302 is captured by jaws 44 and 48 within a cutout 45 disposed within respective jaws 46 and 50.

Lower jaws 44 and 48 may be raised and lowered along respective guide shafts 52 and 54 in ways that are well-known to those of ordinary skill in the art. For example, jaws 44 and 48 may be raised and lowered using an electric solenoid, or a pneumatic actuator (not shown), or jaws 44 and 48 may be raised and lowered mechanically using a motor and a camming mechanism.

In one embodiment of this invention, lower jaws 44 and 48 are raised and lowered mechanically. This embodiment will now be described with particular reference to FIGS. 6 and 7. Each jaw 44 and 48 includes a motor 68 that rotates a cam 70 eccentrically mounted with respect to a motor shaft 72. Bearing 74 on cam 70 rotates about pin 76 and is positioned within a correspondingly formed slide 73 in jaws 44 and 48. Thus, as motor 68 rotates shaft 72, cam 70 raises and lowers jaws 44 or 48 as it moves along slide 73. This configuration causes jaws 44 and 48 to rise rapidly at first and more slowly thereafter.

Each gripper head 24 and 26 includes an associated perspective sensor 60 for locating the front edge of a tab 302 of a magazine 300 when associated gripper 24 or 26 is in a partially retracted position with respect to housing 22. Transport mechanism 100 has been positioned with respect to system 400, and processor 14 has been programmed such that processor 14 knows precisely the distance from gripper head 24 to tab 302 when magazine 300 is disposed within dispensing head 410 and from gripper head 26 to tab 302 for a magazine disposed in supply 200. Sensor 60 preferably has a controlled depth of field so that the presence of tab 302 is only detected when tab 302 is at that known distance from gripper head 24 or 26. Since there are no other objects which are spaced that known distance from gripper heads 24 and 26 when in a predetermined, partially extended position, only detection of a tab 302 at that distance will activate gripper heads 24 and 26. Sensor 60 is preferably a converging diffuse reflective sensor and includes one light emitting diode (LED) 64 which emits a light beam and one photosensor 66. LED 64 and photosensor 66 are each angled or converged toward one another and each includes a focusing lens, so that photosensor 66 only detects light from LED 64 reflected from a surface at a predetermined, known distance from gripper heads 24 and 26 in a defined area of sensitivity. Such converging diffuse reflective sensors are well-known, and are commercially available under product designation EX14A from SunX, Ltd. of Japan. Typically, LED 64 and photosensor 66 are spaced one above the other, to allow location of tab 302 with respect to a vertical or a Z-direction (FIG. 1) to allow proper alignment of gripper heads 24 and 26.

In a preferred embodiment, gripper assembly 20 positions itself above where a gripper head 24 or 26 would expect to detect a tab 302 on a magazine 300 and then begins moving downwardly until the desired sensor 60 detects a tab 302 on a magazine 300, as will be described. Typically, sensor 60 on gripper head 24 is used to position assembly 20 with respect to dispensing head 410. Typically sensor 60 on gripper head 26 is utilized to position assembly 20 with respect to magazine supply 200, as will be described.

Figure 3:
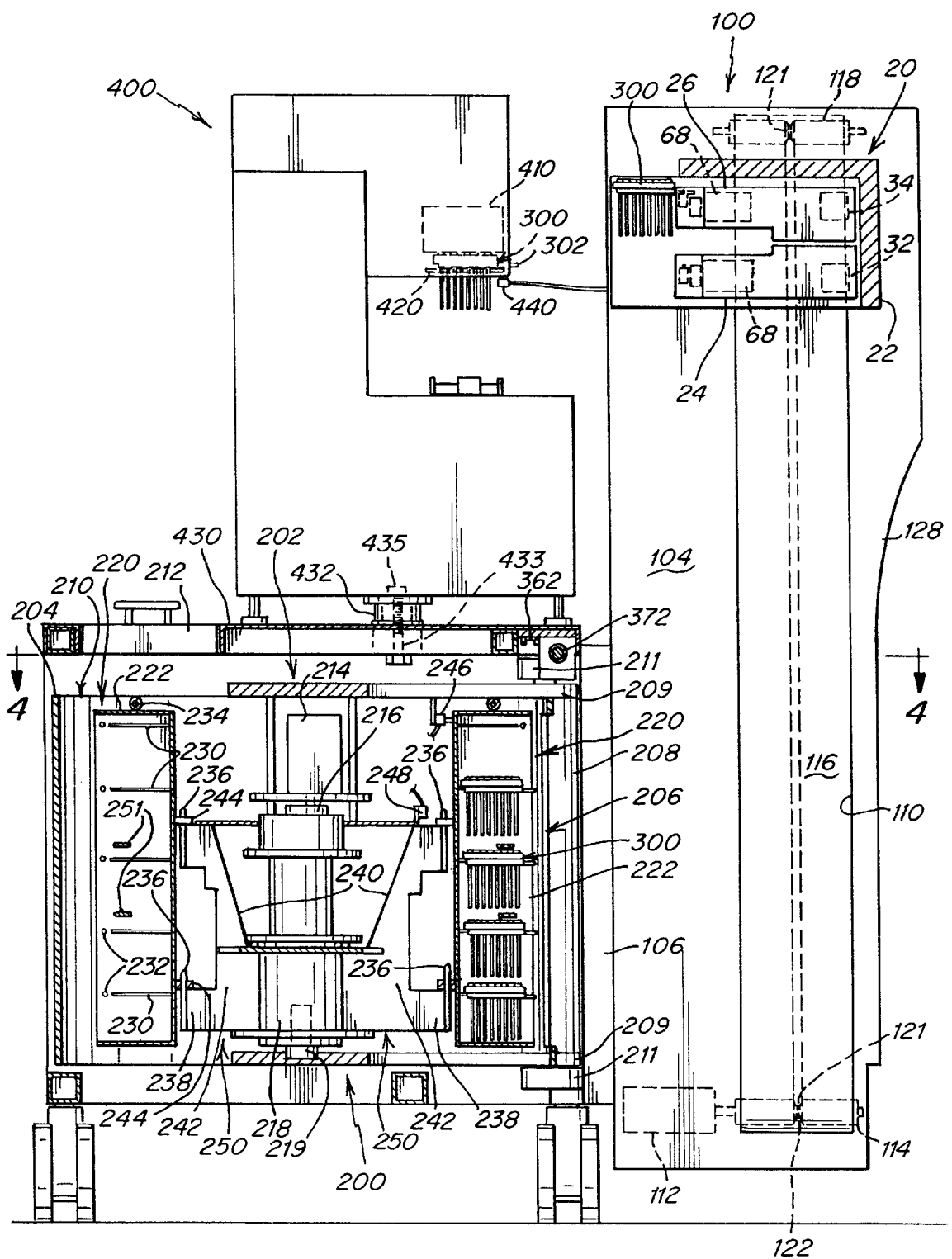
FIG. 3 is a cross-sectional side view taken along the line 3—3 of FIG. 2.

Gripper transport mechanism 100 will now be described with particular reference to FIGS. 3, 4 and 6. Transport mechanism 100 includes a vertical support 104 which is fixedly mounted to table 430 by a bracket 106. Bracket 106 secures transport mechanism 100 such that gripper assembly 20 is aligned with dispensing head 410 in a horizontal or X-direction, and has a known spacing form head 410 in the Y-direction when aligned therewith in the vertical or Z-direction (See FIG. 1). Similarly, bracket 106 assures that gripper assembly 20 has a known spacing in a horizontal or Y-direction from tabs 302 of magazine 300 disposed in magazine supply 200 when gripper assembly 20 is aligned with magazine supply 200 in a vertical or Z-direction. These known locations and distances are programmed into processor 14 to allow proper operation and control of magazine handling apparatus 10.

While gripper transport mechanism 100 may comprise any apparatus suitable for providing the desired vertical motion of gripper assembly 20, in a preferred embodiment, transport mechanism 100 includes a carrier plate 108 which includes or is mounted onto vertical slideways 102 which ride on rails 109. Rails 109 are mounted on or are formed integrally with vertical stiffener 113. Stiffener 113 extends substantially along all of the vertical or Z-direction height of mechanism 100. Gripper assembly 20 is mounted onto plate 108 through plate 111. Supports 130 couple plate 111 to plate 132 on assembly 20. Plate 108 is sufficiently large and of sufficient mass that gripper assembly 20 may be mounted to it at multiple locations to provide precise movement and control of gripper assembly 20. Vertical movement of plate 108 and thus of gripper assembly 20 is provided along rails 109 by a motor 112. Motor 112 drives a grooved or toothed roller 114 which in turn drives a grooved belt 116 which is mounted to carrier plate 108. Belt 116 passes over idler roller 118, and passes on both sides of stiffener 113. Preferably, but not necessarily, opening 110 is covered by belt 116 which moves with plate 108 about rollers 114 and 118. Belt 116 covers the internal operation of transport mechanism 100, and prevents the operator from becoming entangled. Belt 116 may be provided with a V-projection 122 in its center for maintaining alignment of belt 116. A corresponding V-groove 121 is provided in rollers 114 and 118.

In a preferred embodiment, control buttons 126 are provided in a housing 128 on support 104. Buttons 126 may include an emergency stop, a setup selector, a stop button, a reset button and a start button.

Magazine supply 200 will now be described with particular reference to FIGS. 1–4 and 8. It is to be understood that supply 200 may comprise any mechanism capable of supplying clean or unused tip magazines 300 loaded with clean or unused tips 310 for use in dispensing head 410. The following is one embodiment of a suitable supply that may be used in conjunction with the gripper assembly 20 and gripper transport mechanism 100 of this invention.

Figure 4:
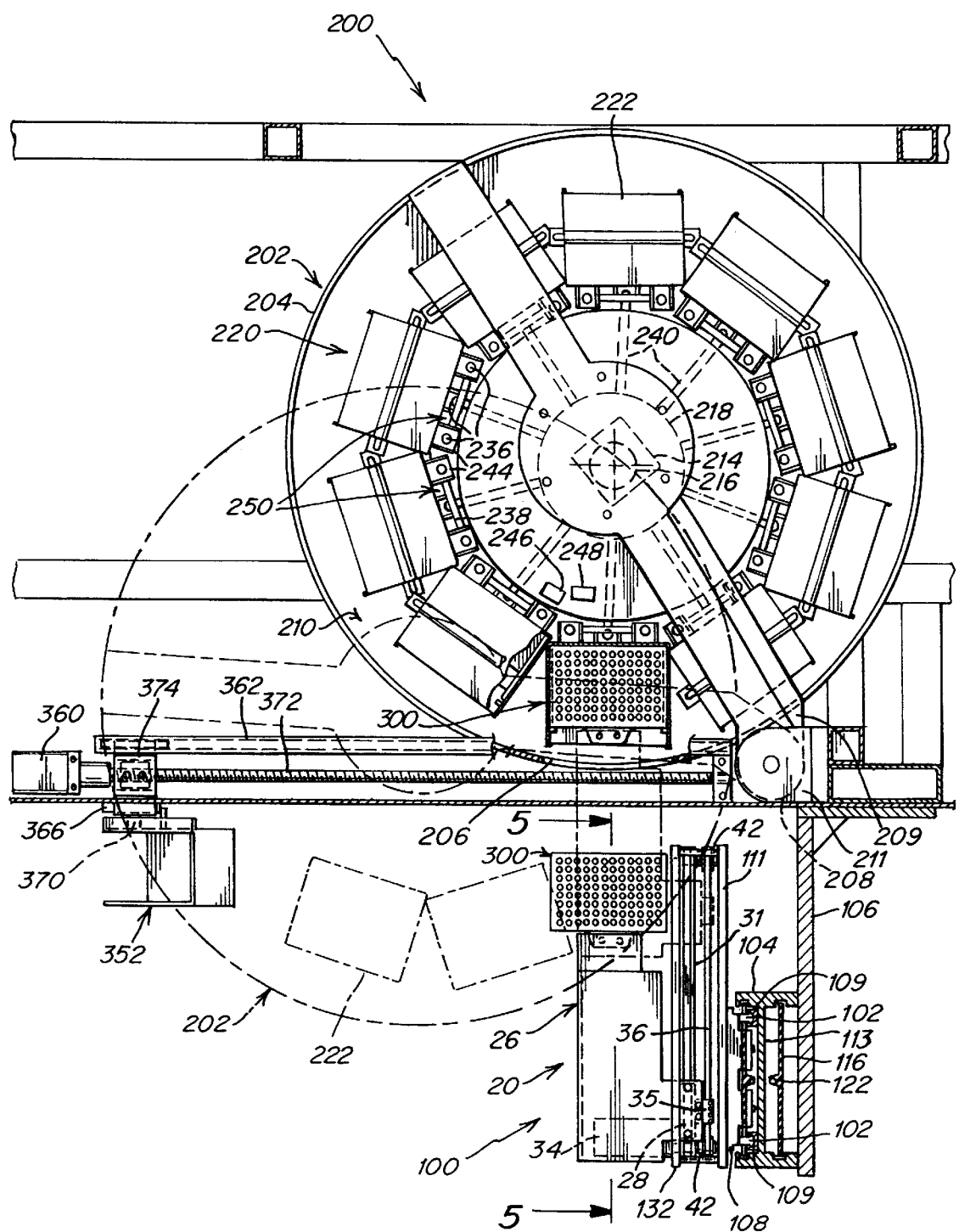
FIG. 4 is a cross-sectional top, plan view taken along the line 4—4 of FIG. 3.

In this embodiment, magazine supply 200 comprises a carousel 202 which is rotatably mounted within housing 204 (See FIG. 4). Housing 204 includes an opening 206 which permits access to magazines 300 within carousel 202. Preferably, although not necessarily, housing 204 is mounted on a post 208 by connectors 209. Post 208 is rotatably mounted on bearings 211 which permit post 208 to be rotated and which allow housing 204 to be pivoted from a position beneath table 430 to an exposed position, as shown in FIG. 4, to allow insertion of magazines 300 into carousel 202 through an opening 210 in the top of housing 204. Opening 210 may also be accessed through a door 212 in table 430, typically behind system 400.

Carousel 202 is rotated within housing 204 about a central axle 218 by a motor 214 which is coupled to carousel 202 by a clutch mechanism 216. Axle 218 is mounted on bearings 219 which permit rotation of axle 218.

Arrayed about axle 218 are a plurality of compartments 220. Typically, although not necessarily, ten compartments 220 are provided. In one embodiment, each compartment is configured to receive a stacker 222. Stackers 222 are configured to contain magazines 300 in a stacked configuration and are removable from associated compartments 220. Each compartment includes a frame 250 that includes rear bracket 240 having a vertically extending, central support 242.

Each stacker 222 typically includes three vertical walls including rear wall 224 and opposed, parallel side walls 228. One side of the stacker has a vertically extending opening 226. Magazines 300 are inserted and withdrawn through opening 226. Disposed on opposed side walls 228 are a series of pairs of aligned rails 230 which are configured to support a magazine body 304 within stacker 222. Each aligned opposed pair of rails 230 disposed on opposed side walls 228 is vertically spaced or spaced in the Z-direction from other opposed pairs of rails 230 a distance sufficient to support a magazine 300 and associated tips 310 depending therefrom without interference with other magazines 300 and associated depending tips 310 disposed above and below. In one embodiment, each stacker 222 is configured to receive five vertically stacked magazines 300. Disposed on an end of each lip facing opening 226 is a detent 232 which prevents magazine 300 from inadvertently sliding out of stackers 222. Stackers 222 may contain one or more horizontal support walls or struts 251 that provide strength and rigidity to stackers 222.

Preferably, each stacker 222 includes a top handle 234 mounted on side walls 228 which allows manual removal of stacker 222 from it's associated compartment 220. Each compartment contains a plurality of upstanding pegs 236 disposed on vertically extending frame members 238. Walls 228 of each stacker 222 include sleeves 244 which correspond to and are aligned with upstanding pegs 236 in compartments 220. Sleeves 244 ride over pegs 236 when stacker 222 is inserted into a compartment 220 through opening 210 to align and hold each stacker 222 in its associated compartment 220. This configuration of pegs 236 and sleeves 244 allows easy and quick insertion, removal and alignment of stackers 222 in associated compartments 220 through opening 210. Each stacker 222 is manually supplied with magazines 300 either while in its compartments 220 or at a location remote from apparatus 10. Stackers 222 are then inserted into carousel 202 as described.

Disposed on carousel 202 are at least two sensors 246 and 248. Sensor 246 determines whether a stacker 222 is disposed in any one compartment 220. If there is no stacker 222 in a compartment 220, motor 214 continues to rotate carousel 202 so that that compartment 220 passes by opening 206 and is not aligned therewith. Motor 214 continues to rotate carousel 202 until sensor 246 detects a stacker 222 in a particular compartment 220. The speed of rotation of carousel 202 is reduced until sensor 248 detects the location of vertical support 242 of the compartment 220 which has already been indicated by sensor 246 to contain a stacker 222. Sensor 248 sends a signal to controller 14 which causes motor 214 to rotate carousel 202 a predetermined, preprogrammed distance, which is the distance from the point where vertical support 242 is sensed by sensor 248 to the point where vertical support 242 is centered within opening 206. At this point, rotation of carousel 202 is stopped, and compartment 220 is aligned with opening 206 such that magazines 300 disposed within associated stacker 222 may be accessed and removed by gripper assembly 20.

When it is desired to withdraw a magazine 300 from carousel 202, gripper assembly 20 is lowered on gripper transport mechanism 100 until gripper assembly 20 is disposed in alignment with the top of opening 206. In a preferred embodiment, sensor 62 on upper gripper head 26 scans opening 206 from the top moving downwardly in a Z-direction (FIG. 1) until it detects a tab 302 on a magazine body 304. At this point, it moves downwardly an additional, predetermined distance to align jaws 48 and 50 of gripper head 26 with tab 302. Gripper head 26 then extends outwardly toward opening 206 along slides 30 a predetermined distance until upper jaw 50 of gripper head 26 is aligned with the top surface 318 of tab 302. At this point, lower jaw 48 is raised so that pins 58 enter into holes 306 and tab 302 is clamped between jaws 48 and 50. At this point, gripper assembly 20 rises up slightly to raise magazine 300 off detents 232, and then magazine 300 thereafter is withdrawn by gripper assembly 20. This process is repeated until all magazines 300 in any one stacker 222 have been removed. When gripper head 26 is positioned to remove the lowermost magazine from a stacker 222, a signal is sent by processor 14 to motor 214 to rotate carousel 202 until the next compartment 220 containing a stacker 222 is aligned with opening 206.

Figure 8:
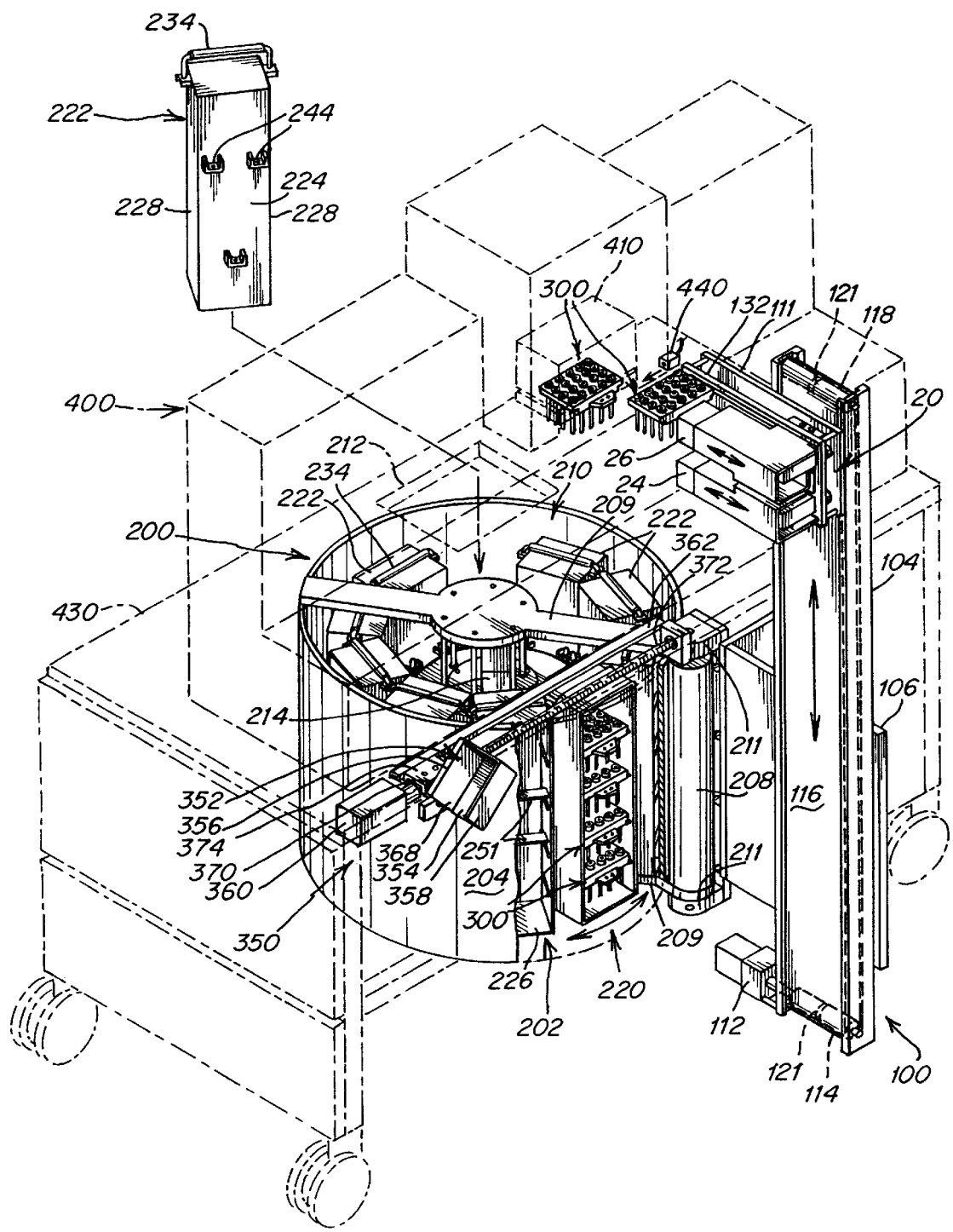
FIG. 8 is a partial, perspective view of the apparatus of FIG. 1 showing the carousel and transport mechanism of this invention.

Disposal mechanism 350 will now be described with particular reference to FIGS. 1, 2 and 8. Disposal mechanism 350 includes a tray 352 having a bottom wall 354, and three side walls 358 which have upper edges 356. An opening 368 is provided at one end of tray 352. A track 362 is provided along table 430. Track 362 extends from about vertical support 104 toward the left side of table 430 as shown in FIG. 1. Block 374 rides on track 362 and is coupled to tray 352 by a pivot coupling 370 which permits tray 352 to ride along track 362. Movement of tray 352 along track 362 is produced by a motor 360 and associated screw drive 372. Disposed along track 362 and adjacent an end thereof on the left side of table 430, as shown in FIG. 9, is a tilt block 366. As tray 352 encounters block 366, tilting of tray 352 about coupling 370 is produced, as drive 372 continues to move tray 352 away from support 104, pivoting tray 352 in a counterclockwise direction about coupling 370 as shown in FIGS. 1 and 8. In this way, magazines 300 with their associated tips 310 are permitted to slide out of tray 352 and into a bin 376 disposed therebelow. Bin 376 may then be removed for disposal of used magazine 300 and tips 310.

With reference now to FIGS. 7–7C and 9A–9J, typical methods of operation of the pipette tip magazine handling apparatus 10 of this invention will now be described. While operation of this apparatus 10 will be described with particular reference to the automated pipetting system of U.S. application Ser. No. 09/865,404, it is to be understood that the apparatus 10 of this invention may be operated with other automated pipetting systems. Moreover, the particular method described with respect to FIGS. 9A–9J represents only an exemplary method of operation of the apparatus 10 of this invention and that this apparatus may be operated in other ways in accordance with this invention by appropriately programming processor 14 as will be apparent to one of ordinary skill in the art.

Figure 9A:
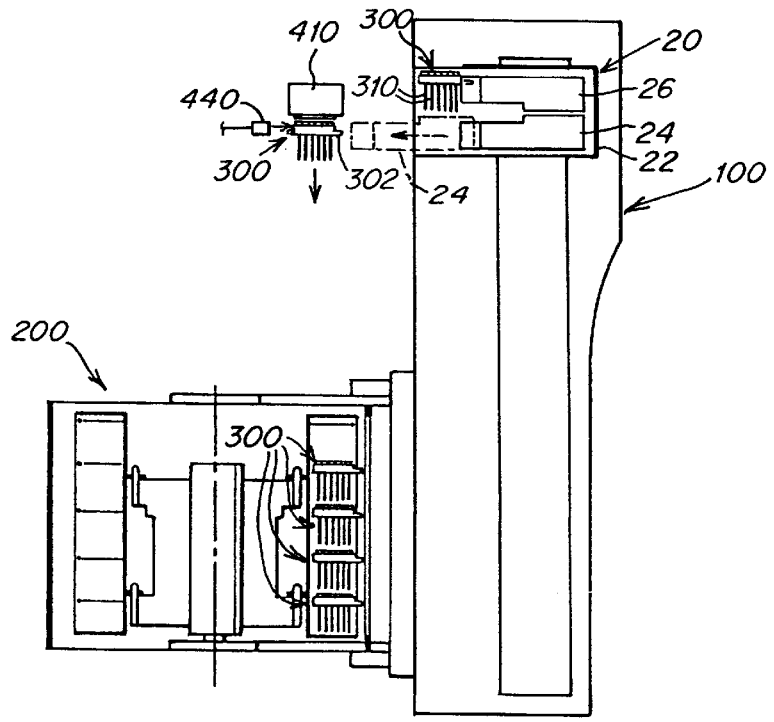
FIG. 9A is a schematic side view of the apparatus of FIG. 1 showing a step in the method of this invention.

Typically, although not necessarily, apparatus 10 commences the cycle by having a clean, unused pipette tip magazine 300 with clean, unused tips 310 being held by gripper head 26, ready for insertion into dispensing head 410, as shown in FIG. 9A. Gripper assembly 20 is positioned on transport mechanism 100 at a location generally even with dispensing head 410 in the Z-direction, as shown in FIG. 9A. Gripper head 26 is retracted into housing 22 awaiting the next step while holding tab 302 on magazine 300 in readiness for inserting magazine 300 into dispensing head 410. This position is considered the "remove scan position". In this position, lower gripper head 24 is disposed generally above clamp 420 and above tab 302 of magazine 300 disposed in dispensing head 410. Lower gripper head 24 is extended a short distance from housing 22 into a scan position in which it looks for a tab 302 on a magazine 300 disposed in dispensing head 410. (See FIG. 7) Gripper head 24 is approximately 10 inches from housing 22 and 2 inches from dispensing head 410, in a preferred embodiment. In this position, if there is a magazine 300 in dispensing head 410, tab 302 is within the sensing range or depth of field of the sensor 60 on gripper head 24 and will be sensed by sensor 60 as gripper assembly 20 begins its preprogrammed scan movement downwardly in the Z-direction along gripper transport mechanism 100. If there is a magazine 300 in dispensing head 410, tab 302 will be sensed. Once tab 302 has been detected, the gripper assembly 20 lowers a preprogrammed amount so that the gripper head 24 is exactly aligned with tab 302. The processor 14 knows the exact distance between the sensor 60 and jaws 44 and 46. At this point, if the pipetting operation is still in progress and clamp 420 is closed, gripper assembly 20 remains stationary and waits until the pipetting operation has been completed.

Figure 7A:
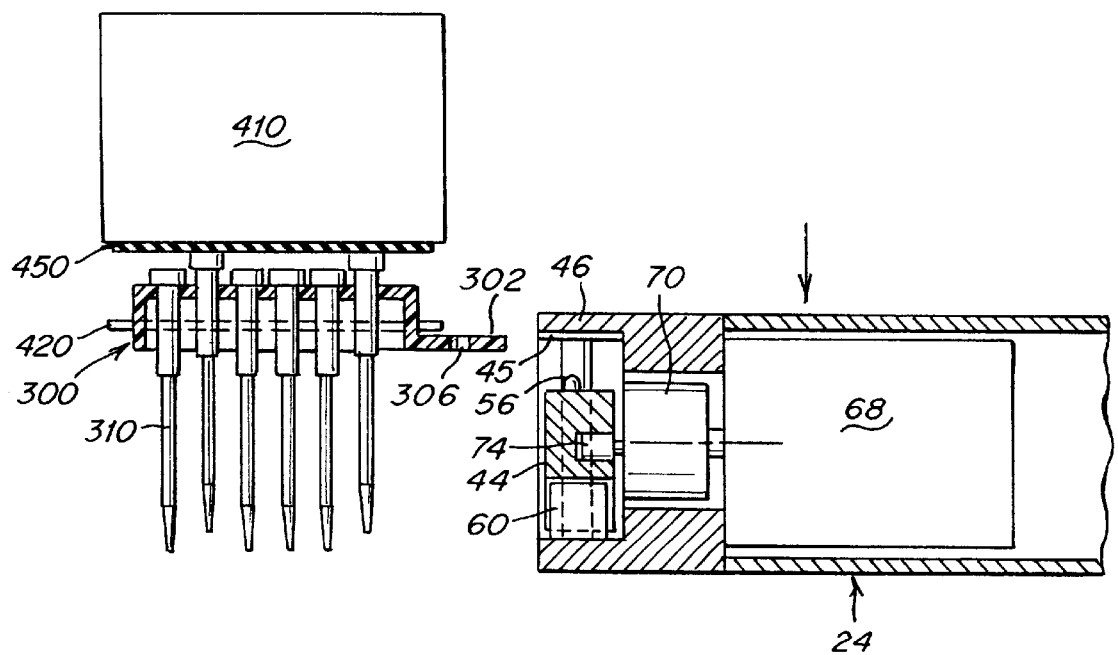
FIG. 7A is a cross-sectional side view of the gripper head of FIG. 7 showing one step in the operation thereof.
Figure 9B:
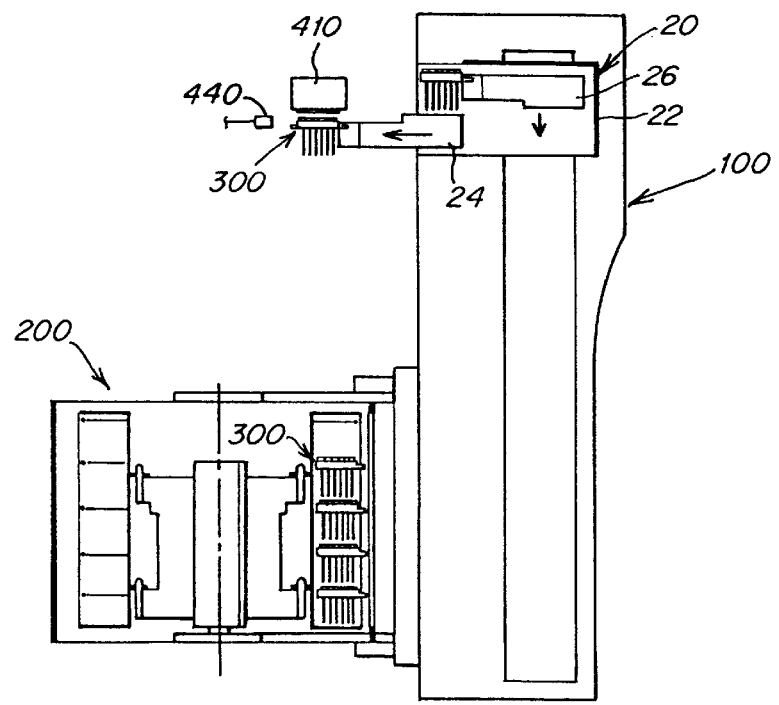
FIG. 9B is a schematic side view of the apparatus of FIG. 1, showing another step in the method of this invention.
Figure 9C:
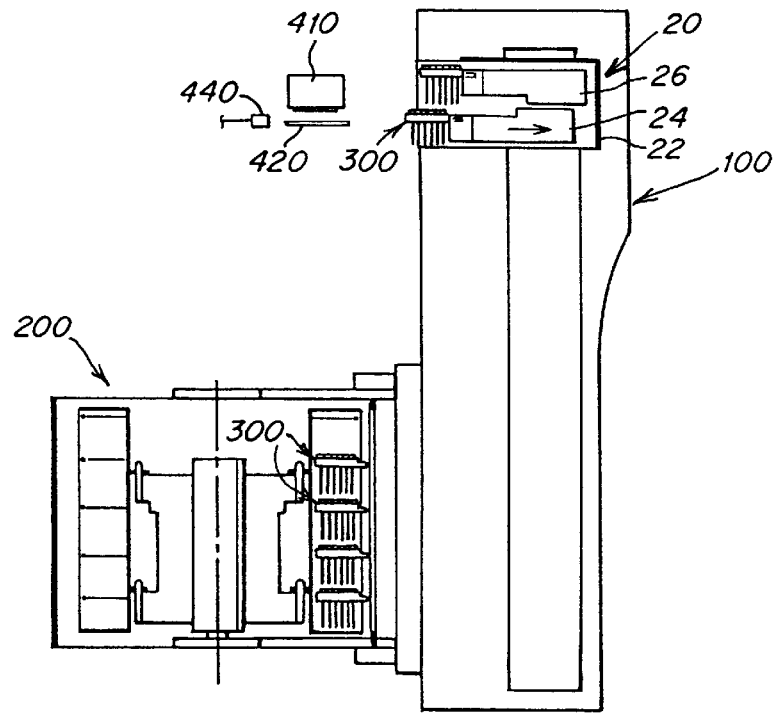
FIG. 9C is a schematic side view of the apparatus of FIG. 1 showing another step in the method of this invention.

Once sensor 440 sends a signal to processor 14 that clamp 420 is in its open position, indicating completion of the pipetting operation, gripper head 24 is extended from housing 22 toward magazine 300 in dispensing head 410, as shown in FIG. 9B. At the same time, jaw 44 is lowered with respect to jaw 46, so that jaws 44 and 46 are able to accept tab 302 (See FIG. 7A). Once tab 302 resides between jaws 44 and 46, jaw 44 is raised with respect to jaw 46 to extend pins 56 through holes 306 in tab 302 to clamp tab 302.

Figure 7B:
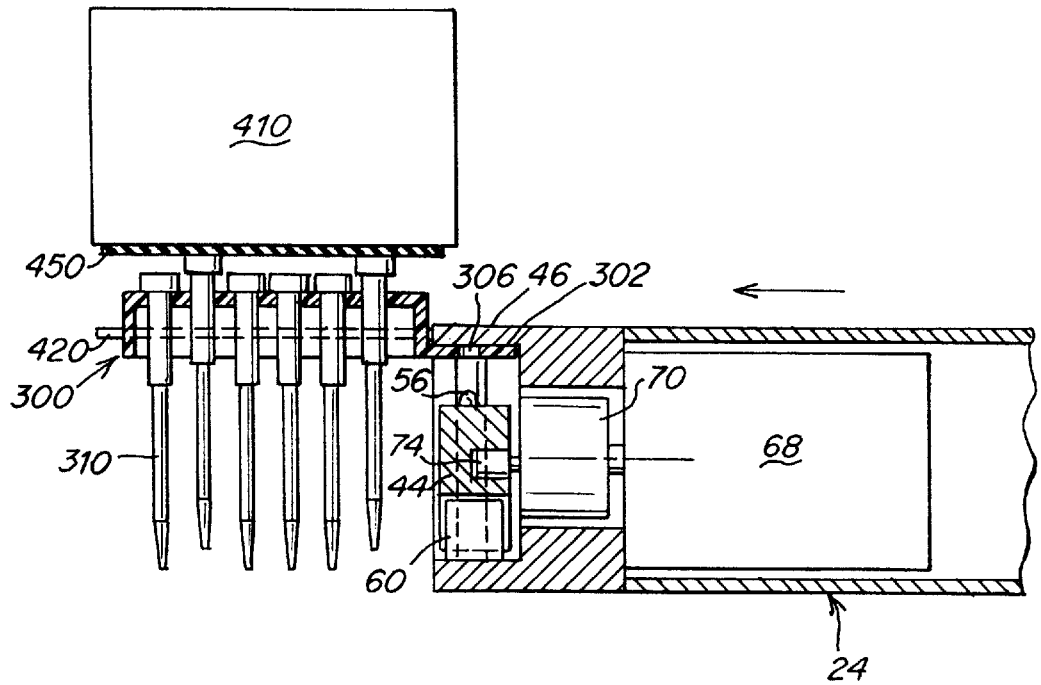
FIG. 7B is a cross-sectional side view of the gripper head of FIG. 7 showing another step in the operation thereof.
Figure 7C:
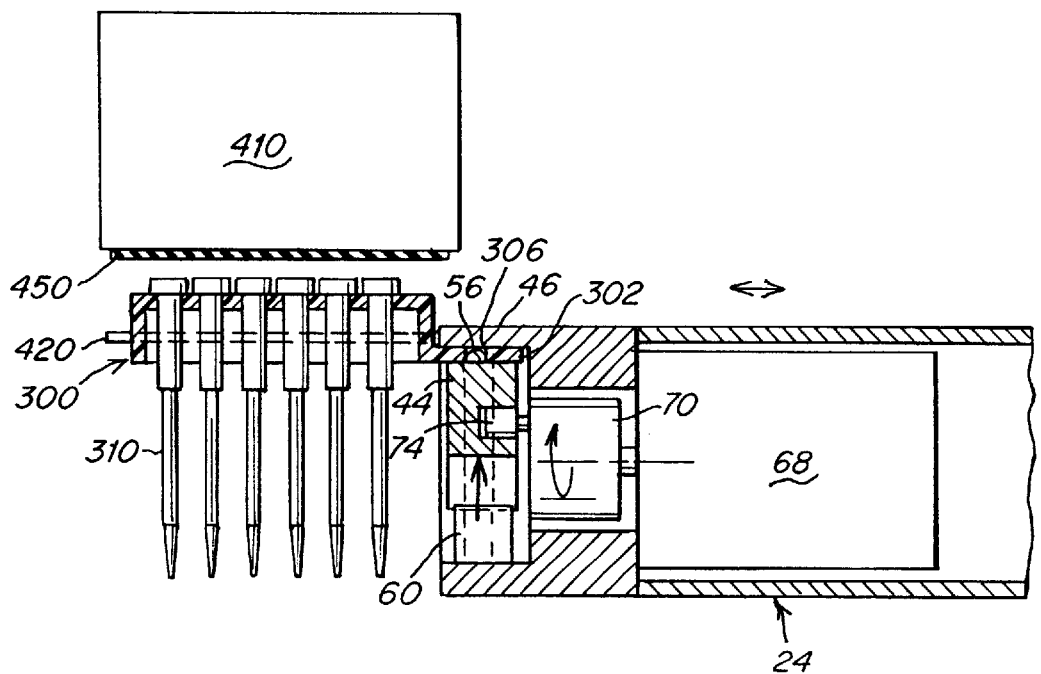
FIG. 7C is a cross-sectional side view of the gripper head of FIG. 7 showing another step in the operation thereof.

In one embodiment, magazine 300 is simply withdrawn horizontally in the Y-direction from dispensing head 410. However, in an alternative embodiment of the method of this invention, motor 112 is first activated to lower assembly 20 a small amount to move magazine 300 downwardly in the Z-direction with respect to dispensing head 410, as shown in FIG. 7B. This downward movement is performed to withdraw the pipette tips 310 out of sealing engagement with a seal 450 or nozzles (not shown) that may be present in dispensing head 410. Should the downward movement be insufficient to break the seal between the upper end 314 of tips 310 and the dispensing head, whether it be a silicone seal 450 or nozzle ends (not shown), motor 32 is activated to produce oscillating horizontal movement of gripper head 24 and thus magazine 300 in a Y-direction into and out of dispensing head 410, as shown in FIG. 7C. This horizontal oscillating movement further serves to break any seal that may exist between upper end 314 of tip 310 and seal 450 or nozzle ends in the dispensing head 410. Thereafter, the used magazine 300 and associated tips 310 are withdrawn from dispensing head 410 toward housing 22, as shown in FIG.

9C. However, preferably, magazine 300 is only withdrawn part of the way toward housing 22, and remains in a position such that gripper head 24 grasps magazine 300 at a location somewhat spaced in the Y-direction from housing 22.

If sensor 60 does not detect a tab 302 of a magazine 300 within dispensing head 410, apparatus 10 skips the withdrawal step described above and goes directly to the insertion step described below in which gripper head 26 inserts an unused magazine into dispensing head 410.

Figure 9D:
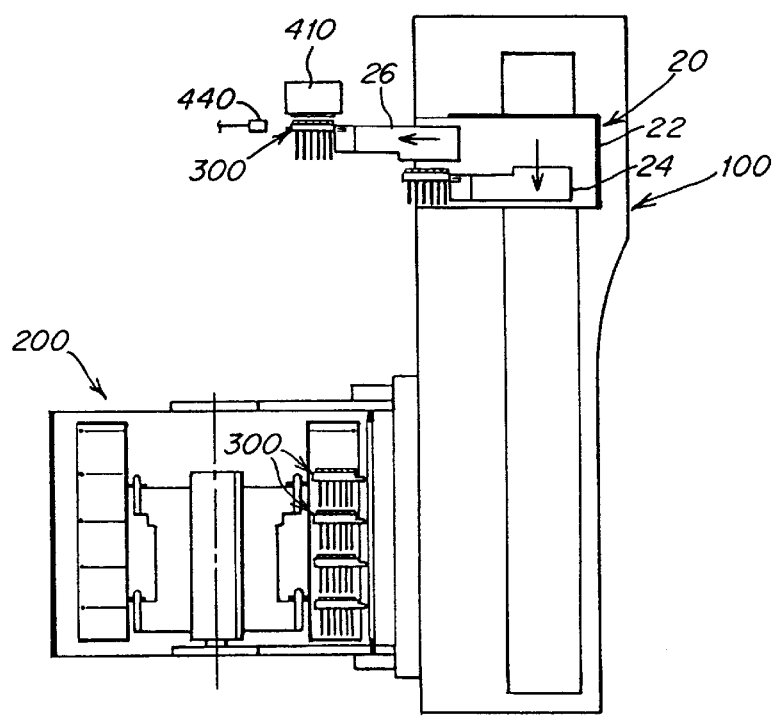
FIG. 9D is a schematic side view of the apparatus of FIG. 1 showing another step in the method of this invention.

Processor 14 has been preprogrammed, so that once the used magazine 300 has been withdrawn, stepper motor 112 is activated to lower assembly 20 to a precise position so that the new magazine 300 containing unused tips 310 in gripper head 26 is now aligned with dispensing head 410. Motor 34 is then activated to extend gripper head 26 to insert the unused magazine 300 into clamp 420 of dispensing head 410, as shown in FIG. 9D. Once automated pipetting system 400 detects that an unused magazine 300 is disposed within clamp 420, clamp 420 is automatically closed by system 400 to grasp unused magazine 300. Sensor 440 then provides a signal to processor 14 indicating that clamp 420 is in a closed position. Thereafter, jaws 44 and 46 are opened and processor 14 sends a signal to motor 34 to retract gripper head 26 within housing 22.

Figure 9E:
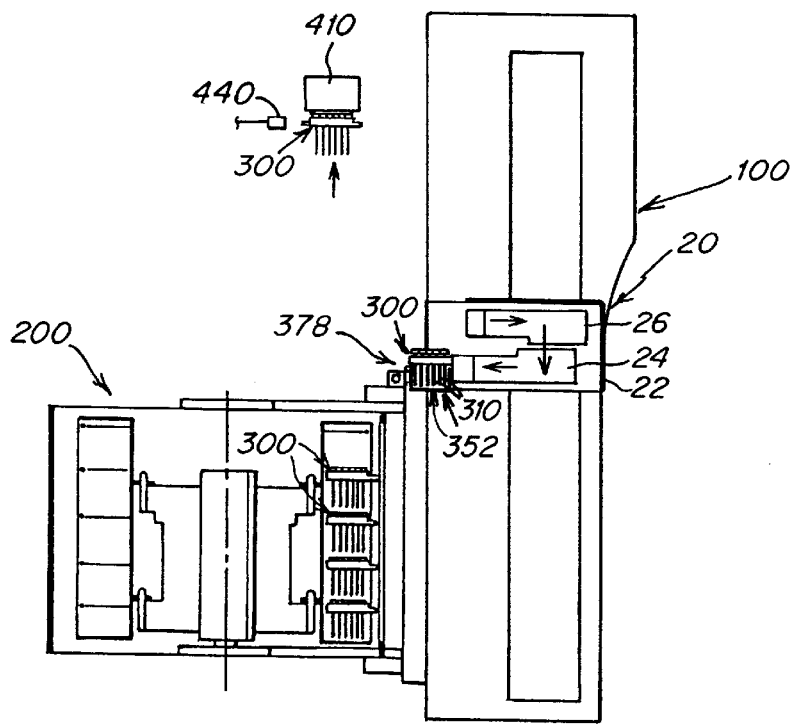
FIG. 9E is a schematic side view of the apparatus of FIG. 1 showing another step in the method of this invention.
Figure 9F:
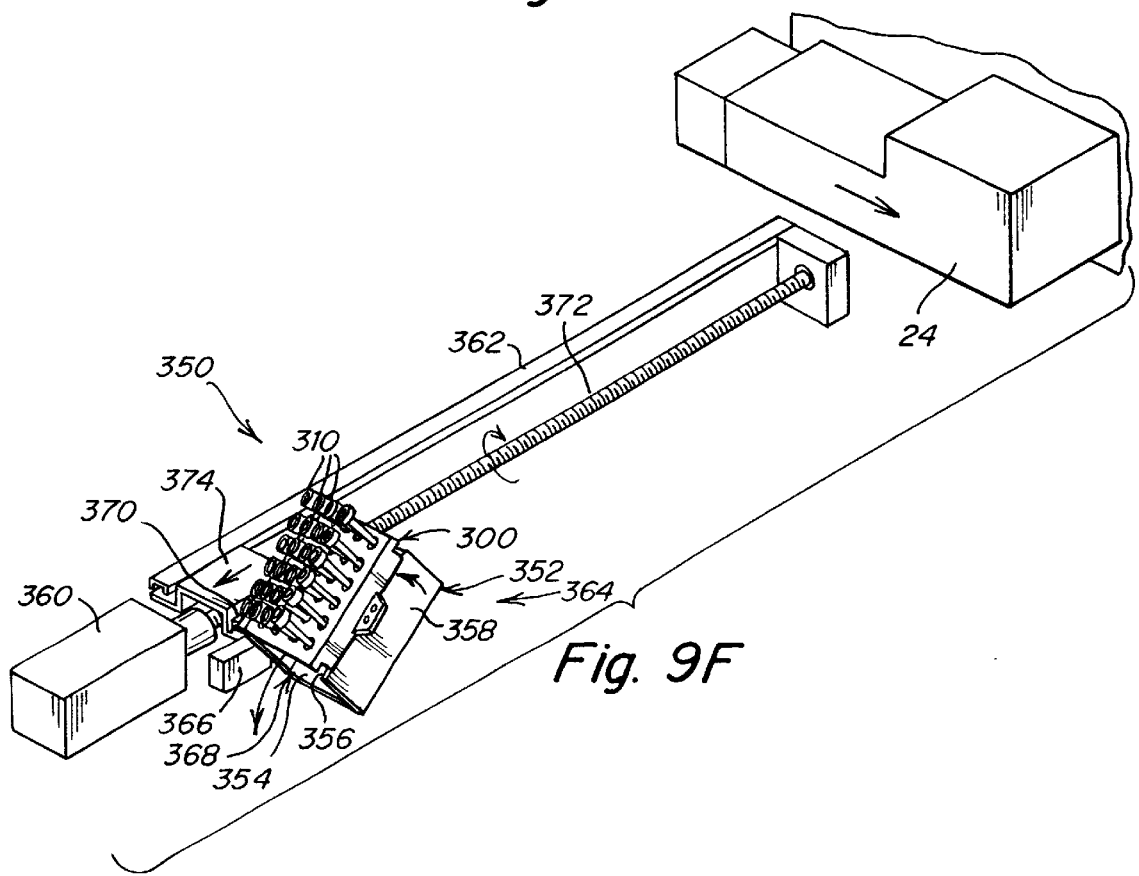
FIG. 9F is a partial, schematic view of a portion of the apparatus of FIG. 1 showing another step in the method of this invention.
Figure 9G:
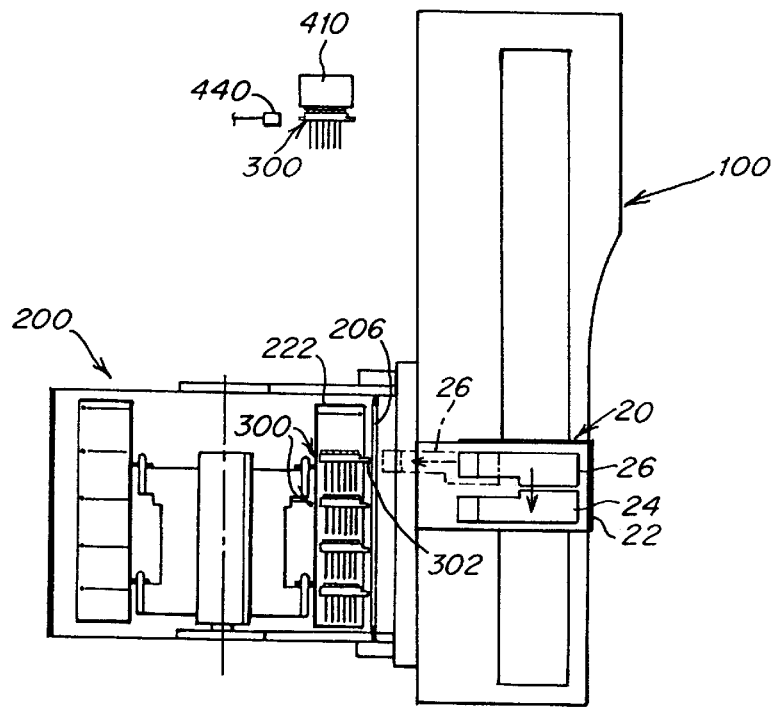
FIG. 9G is a schematic side view of the apparatus of FIG. 1 showing another step in the method of this invention.

After a used magazine 300 with used tips 310 has been withdrawn from dispensing head 410, gripper assembly lowers automatically to disposal mechanism 350. Processor 14 has been preprogrammed to know the distance that gripper assembly 20 must be lowered in the Z-direction so that used magazine 300 is aligned with dump tray 352, as shown in FIG. 9E. Dump tray 352 already has been moved by processor 14 to a receiving location 378 so that tray 352 is aligned with gripper head 24 in a Y-direction. As assembly 20 is lowered by transport mechanism 100, used tips 310 and magazine 300 drop directly onto tray 352. The lower ends 316 of tips 310 rest on bottom wall 354 of tray 352, while magazine 300 sits on upper edge 356 of sidewalls 358. Jaw 44 then lowers with respect to jaw 46 to release tab 302, and gripper head 24 is retracted back into housing 22, leaving magazine housing 300 and tips 310 sitting in tray 352. Thereafter, motor 360 is activated to move tray 352 to the left, as shown in FIG. 1, or in a direction away from transport mechanism 100 along tracks 362 to a dump position 364. In dump position 364, tray 352 strikes a tilt block 366, causing tray 352 to tilt downwardly to the left, or in a counterclockwise direction, as shown in FIG. 9F, or into a dump position 364 where tilt block 366 is positioned. Once tray 352 strikes tilt block 366, tray 352 tilts so that open end 368 faces downwardly. Used magazine 300 and associated tips 310 slide out of tray 352 through open end 368 under the influence of gravity and into bin 376. Thereafter, tray 352 remains in this position, until another used magazine 300 is withdrawn from dispensing head 410. It will be apparent, that this step is skipped if no used magazine 300 is withdrawn from head 410.

Figure 9H:
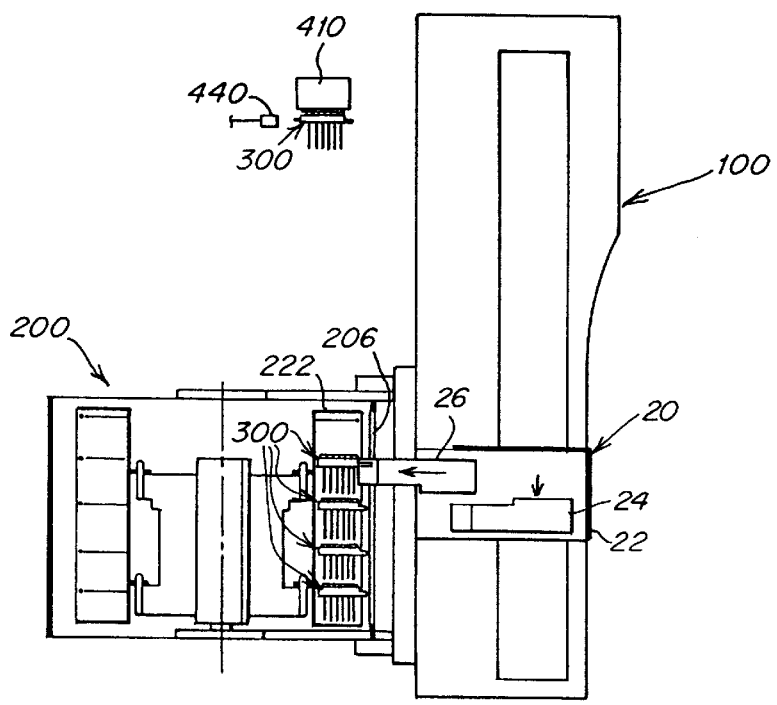
FIG. 9H is a schematic side view of the apparatus of FIG. 1 showing another step in the method of this invention.
Figure 9I:
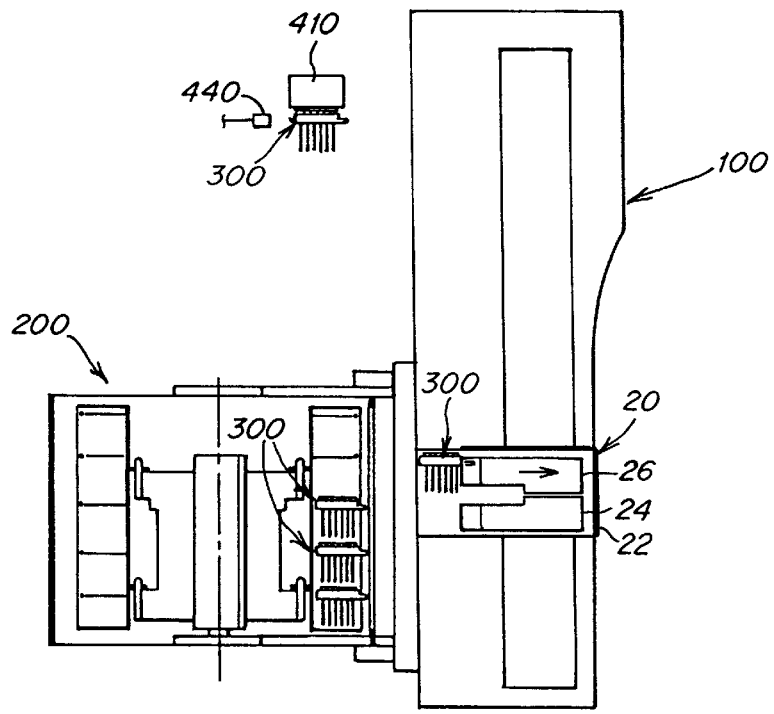
FIG. 9I is a schematic, side view of the apparatus of FIG. 1 showing another step in the method of this invention.
Figure 9J:
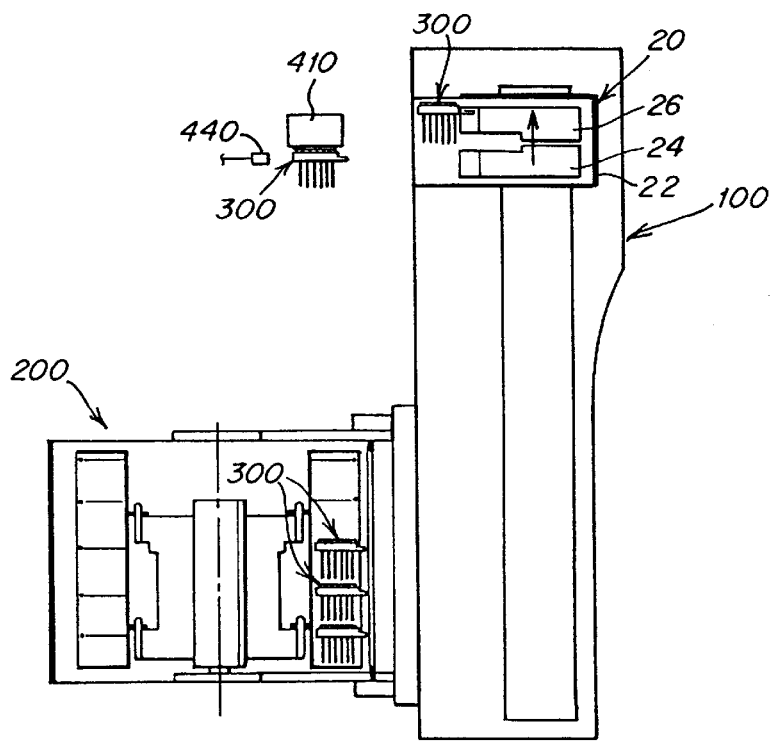
FIG. 9J is a schematic, side view of the apparatus of FIG. 1 showing another step in the method of this invention.

In the next step of this method, assembly 20 is lowered to retrieve a new, unused magazine 300 from magazine supply 200, as shown in FIG. 9H. In this step, assembly 20 is lowered a preprogrammed amount so that gripper head 26 is positioned at the top edge of carousel 202 and in alignment with opening 206. Motor 112 then moves assembly 20 downwardly past opening 206 in a scan mode in which sensor 62 looks for a tab 302 on an unused magazine 300 in compartment 220. In this position, gripper head 26 is spaced a predetermined distance from carousel 202, so that a tab 302, on any magazine 300 within compartment 220, is within the depth of field of sensor 62. Assembly 20 continues to move downwardly, until a tab 302 is sensed. Assembly 20 then drops a predetermined amount so that jaws 48 and 50 are is aligned with the sensed tab 302. Gripper head 26 is then extended by motor 34, and jaw 48 is lowered with respect to jaw 50, as shown in FIG. 9H. Tab 302 is then grasped by raising jaw 48 with respect to jaw 50. Assembly 20 is raised slightly to lift magazine 300 over detents 232. Thereafter, gripper head 26 and magazine 300 are withdrawn from carousel 202, as shown in FIG. 9I. Assembly 20 is then raised into its initial position in which assembly 20 is aligned with dispensing head 410 as previously discussed, as shown in FIG. 9J.

The next time gripper head 26 is lowered to select an unused magazine 300 from carousel 202, it will select the next lower magazine 300 within the particular stacker 222 removed when gripper head 26 is lowered to the lowest level of carousel 202 for selection of the lowest magazine 300. When gripper 26 is detected as having selected a magazine 300 at this level, a processor 14 sends a signal to motor 214 which indexes carousel 202 to the next compartment containing a stacker 222. Typically, carousel 202 is rotated in a counterclockwise direction, although it could be rotated in a clockwise direction. If the next adjacent compartment 220 in a clockwise direction contains no stacker 222, carousel 202 continues to rotate. The presence or absence of a stacker is detected by sensor 246. Carousel 202 will continue to rotate until a stacker 222 is detected. Thereafter, rotation is slowed, and the carousel is automatically rotated a predetermined amount once spine 242 has been detected by sensor 248 to align opening 226 in the stacker 222 with opening 206 in housing 204. Thereafter, the process is repeated for withdrawing an unused magazine 300 from carousel 202. If no compartments 220 contain stackers 222, a signal will be sent to the operator that additional magazines are required.

When power is on, clutch 216 is engaged, to prevent unwanted rotation of carousel 202. Once power is turned off, carousel 202 is free-wheeling to allow easy positioning of carousel 202 to allow manual insertion or withdrawal of stackers 222 from compartments 220. As indicated, stackers 222 may be inserted and withdrawn from compartments 220 either by pivoting housing 204 into the position shown in FIG. 4, or by inserting or withdrawing the stackers 222 through door 212. Typically, stackers 222 are manually loaded with unused magazines 300 at another location.

All of the motors and chain drives described in this application are conventional and are well known to those of ordinary skill in the art. In one embodiment, some or all of the motors described herein are closed loop stepper motors.

It will be appreciated that, instead of a table 430, a laboratory bench or other like support may be used for pipetting system 400. All that is required is precise positioning of system 400 with respect to magazine handling apparatus 10 and magazine supply 200.

While preferably, a separate processor 14 is utilized for magazine handling apparatus 10 and a separate processor (not shown) is used for automated pipetting system 400, it will be appreciated, that a single processor or personal computer could be used for both systems. In the embodiment described above, the only electrical connection between system 400 and apparatus 10 is sensor 440 which is disposed on clamp 420 and which has an electrical connection with processor 14. However, sensor 440 could be coupled to a processor for a system 400, which in turn could communicate with processor 14. In this way, system 400 could be integrated with system 10, as opposed to the two separate, stand alone systems described herein.

Modifications and improvements within the scope of this invention will occur to those skilled in the art. The above description is intended to be exemplary only. The scope of this invention is defined only by the following claims and their equivalents.

What is claimed is:

1. Apparatus for inserting and withdrawing from an automated pipettor magazines containing a plurality of pipette tips, said apparatus comprising:
    a source of unused or cleaned magazines and unused or cleaned pipette tips;
    a first head for gripping and retrieving a used magazine with used pipette tips from the pipettor and for disposing of the used magazine and used tips;
    a second head for retrieving an unused or cleaned magazine with unused or cleaned tips from the source of unused or cleaned magazines and tips and for inserting the unused or cleaned magazines with unused or cleaned tips into the pipettor for replacing the used magazine and used pipette tips; and
    a transport for transferring a used magazine with used tips away from the pipettor, and for retrieving an unused or cleaned magazine with unused or cleaned tips from the source of unused or cleaned magazines and tips.

2. The apparatus of claim 1 further comprising a tray for receiving used magazines and pipette tips from the first head, and for transporting the used magazines and pipette tips from the first head to a disposal location.

3. The apparatus of claim 1 wherein said source of unused or cleaned magazines and unused or cleaned pipette tips comprises:
    a carousel having a plurality of compartments containing unused or cleaned magazines carrying unused or cleaned tips; and
    a motor for rotating the carousel to position a selected one of said compartments adjacent an opening for removal of unused or cleaned magazines and tips from the selected compartment.

4. The apparatus of claim 3 further comprising a plurality of stackers, each of said stackers being insertable and removable from said compartments.

5. The apparatus of claim 4 wherein each of said stackers comprises:
    at least two spaced, opposed walls that are generally parallel to one another;
    an opening disposed between said two walls through which magazines may be accessed; and
    at least one pair of spaced, aligned, generally parallel rails, one of said pair of rails being disposed on one of said walls, and the other of said pair of rails being disposed on the other of said walls for supporting a magazine within said stacker.

6. The apparatus of claim 4 wherein each stacker further comprises a handle for removal of said stacker.

7. The apparatus of in claim 4 further comprising:
    a first sensor for sensing whether a compartment contains a stacker; and
    a second sensor for positioning the detected stacker in alignment with the opening in said carousel.

8. The apparatus of claim 1 wherein the first and second heads comprise at least one sensor for detecting the existence of a feature on a pipetting tip magazine.

9. The apparatus of claim 8 wherein said sensor has a controlled depth of field that will only detect the presence of a magazine if the feature is detected within the controlled depth of field.

10. The apparatus of claim 1 wherein said second head is not disposed below said first head.

11. The apparatus of claim 10 wherein said second head is disposed above said first head.

12. The apparatus of claim 1, wherein the source of unused or cleaned magazines and unused or cleaned pipette tips is disposed below and generally in alignment with the pipettor in a vertical direction.

13. The apparatus of claim 1, wherein the transport moves the first and second heads in a generally vertical direction.

14. The apparatus of claim 13, wherein the transport includes generally vertical slideways.

15. Apparatus for inserting and withdrawing from an automated pipettor magazines containing a plurality of pipette tips, said apparatus comprising:
    at least one gripping head for retrieving a used magazine containing used pipette tips from the pipettor and for replacing the used magazine and used pipette tips in the pipettor with another unused or cleaned magazine with unused or cleaned pipette tips;
    a source of unused or cleaned magazines and unused or cleaned pipette tips;
    a transport for transferring a used magazine with used tips away from the pipettor, and for retrieving an unused or cleaned magazine with unused or cleaned tips from the source of unused or cleaned magazines and tips; and
    a tray for receiving used magazines and pipette tips from the at least one gripping head, and for transporting the used magazines and pipette tips from the gripping head to a disposal location.

16. Apparatus for inserting and withdrawing from the dispensing head of an automated pipettor magazines containing a plurality of pipette tips, said apparatus comprising:
    at least one gripping head for retrieving a used magazine containing used pipette tips from the dispensing head, and for replacing the used magazine and used pipette tips in the dispensing head with another unused or cleaned magazine with unused or cleaned pipette tips;
    a source of unused or cleaned magazines and unused or cleaned pipette tips; and
    a transport for transferring a used magazine with used tips away from the dispensing head of the pipettor, and for retrieving an unused or cleaned magazine with unused or cleaned tips from the source of unused or cleaned magazines and tips.

17. The apparatus of claim 16, wherein the at least one gripping head moves in a generally horizontal direction for retrieving the used magazine containing used pipette tips and for replacing the used magazine and used pipette tips in the dispensing head with another unused or cleaned magazine with unused or cleaned pipette tips.

18. The apparatus of claim 16, wherein the source of unused or cleaned magazines and unused or cleaned pipette tips is disposed below and generally in alignment with the dispensing head in a vertical direction.

19. The apparatus of claim 18, wherein the transport moves said at least one gripping head only in a generally vertical direction.

20. The apparatus of claim 16, wherein the at least one gripping head comprises:
    a first head for gripping and retrieving a used magazine with used pipette tips from the dispensing head and for disposing of the used magazine and used tips; and
    a second head for retrieving an unused or cleaned magazine with unused or cleaned tips from the source of unused or cleaned magazines and tips and for inserting the unused or cleaned magazines with unused or cleaned tips into the dispensing head of the pipettor.

21. The apparatus of claim 20, wherein the second head is not disposed below the first head.

22. The apparatus of claim 21, wherein the second head is disposed above the first head.

23. In combination:

an automated pipettor comprising:
  a dispensing head; and
  a clamp for securing a magazine containing a plurality of pipette tips within the dispensing head;

at least one gripping head for retrieving from the clamp of the pipettor a used magazine containing used pipette tips and for replacing the used magazine and used pipette tips in the clamp with another unused or cleaned magazine with unused or cleaned pipette tips;

a source of unused or cleaned magazines and unused or cleaned pipette tips;

a transport for transferring a used magazine with used tips away from the clamp in the pipettor and for retrieving an unused or cleaned magazine with unused or cleaned tips from the source of unused or cleaned magazines and tips.

\* \* \* \* \*